(12) United States Patent
Williams et al.

(10) Patent No.: US 6,325,768 B1
(45) Date of Patent: Dec. 4, 2001

(54) GLOVE FOR MAKING GONIOMETRIC MEASURES

(75) Inventors: Nicholas Williams, Leeds; Justin Miles Tristan Penrose, Sheffield; Robin Hollands, Sheffield; Anthony Trevor Barker, Sheffield, all of (GB)

(73) Assignee: The University of Sheffield, Sheffield (GB)

( * ) Notice: Subject to any disclaimer, the term of this patent is extended or adjusted under 35 U.S.C. 154(b) by 0 days.

(21) Appl. No.: 09/194,001

(22) PCT Filed: May 19, 1997

(86) PCT No.: PCT/GB97/01382

§ 371 Date: Apr. 15, 1999

§ 102(e) Date: Apr. 15, 1999

(87) PCT Pub. No.: WO97/43953

PCT Pub. Date: Nov. 27, 1997

(30) Foreign Application Priority Data

May 18, 1996 (GB) .................................................. 9610568

(51) Int. Cl.$^7$ ...................................................... A61B 5/00
(52) U.S. Cl. ............................................................. 600/595
(58) Field of Search ................................... 600/587, 595; 223/78

(56) References Cited

U.S. PATENT DOCUMENTS

| | | | |
|---|---|---|---|
| 4,444,205 | * | 4/1984 | Jackson ................................ 600/595 |
| 4,542,291 | | 9/1985 | Zimmerman .......................... 250/231 |
| 4,757,453 | * | 7/1988 | Nasiff ................................... 600/595 |
| 4,986,280 | * | 1/1991 | Marcus et al. ........................ 600/595 |
| 4,988,981 | | 1/1991 | Zimmerman et al. ................ 340/709 |
| 5,047,952 | | 9/1991 | Kramer et al. ........................ 364/513 |
| 5,086,785 | | 2/1992 | Gentile et al. ........................ 128/782 |
| 5,143,505 | * | 9/1992 | Burdea et al. ........................... 414/5 |
| 5,280,265 | | 1/1994 | Kramer et al. ........................ 338/210 |
| 5,316,017 | * | 5/1994 | Edwards et al. ...................... 600/595 |
| 5,442,729 | | 8/1995 | Kramer et al. ......................... 395/2.8 |
| 5,482,056 | | 1/1996 | Kramer ................................ 128/782 |
| 5,592,401 | | 1/1997 | Kramer ................................ 364/550 |

FOREIGN PATENT DOCUMENTS

| | | |
|---|---|---|
| WO 89/07905 | 9/1989 | (WO) . |
| WO 94/01042 | 1/1994 | (WO) . |
| WO 94/09727 | 5/1994 | (WO) . |
| PCT/GB 97/01382 | 5/1997 | (WO) . |

OTHER PUBLICATIONS

Sam Wise, et al. "Evaluation of a fiber optic glove for semi-automated goniometric measurements", Journal of Rehabilitation Research and Development, vol. 27, No. 4, pp. 411–424, 1990.

* cited by examiner

Primary Examiner—Max Hindenburg
(74) Attorney, Agent, or Firm—Fish & Richardson P.C.

(57) ABSTRACT

The invention relates to a glove for making goniometric measures, i.e. angular measurements, of a wearer's hand and a method of manufacture of the same. The glove is adapted for use in the assessment of ahnad mobility in medical applications and is particularly useful for misshaped hands. The glove comprises a palmar panel with finger sections extending short of the distal interphalangeal joint and preferably proximal to the distal interphalangeal joint.

30 Claims, 8 Drawing Sheets

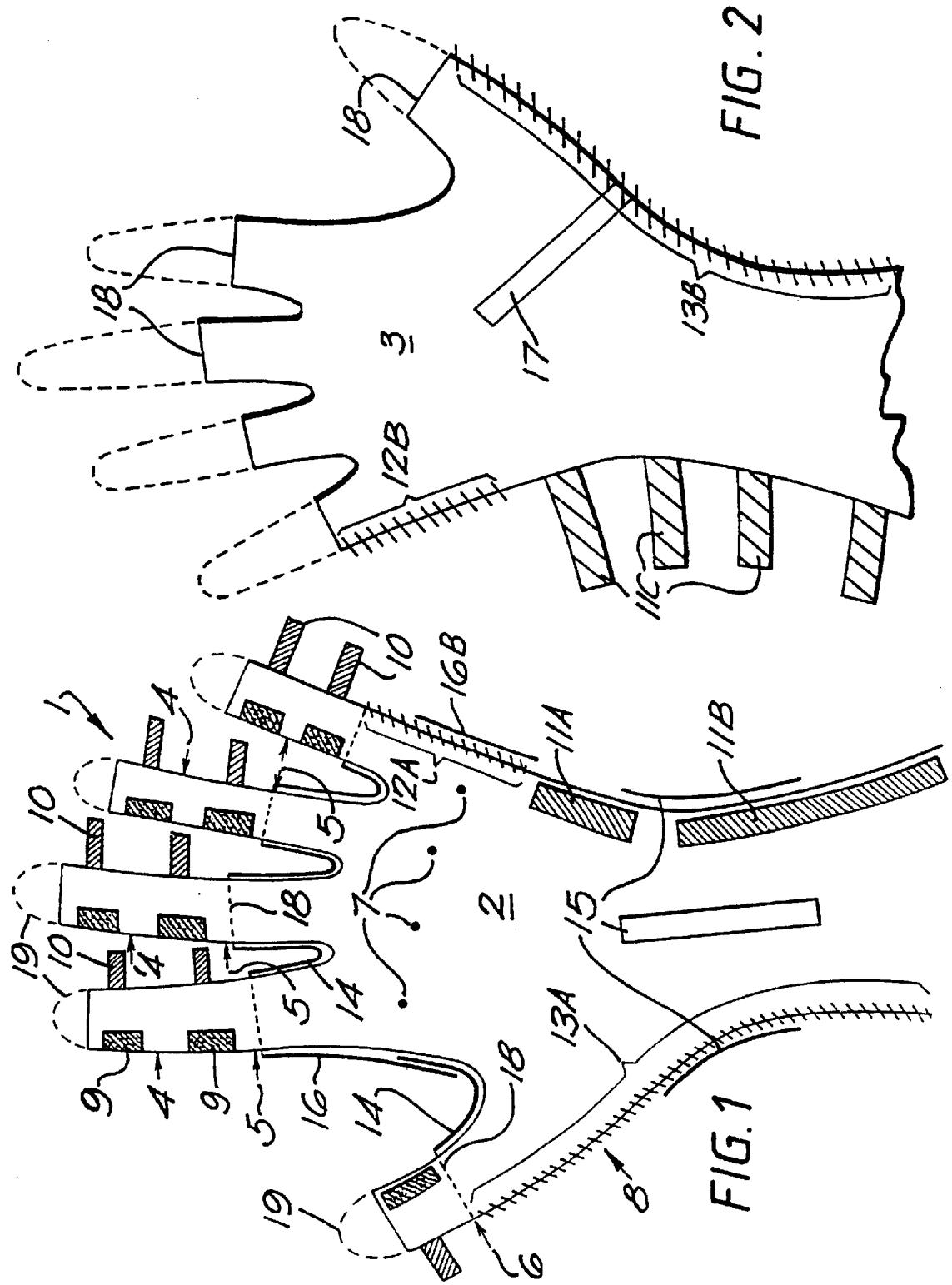

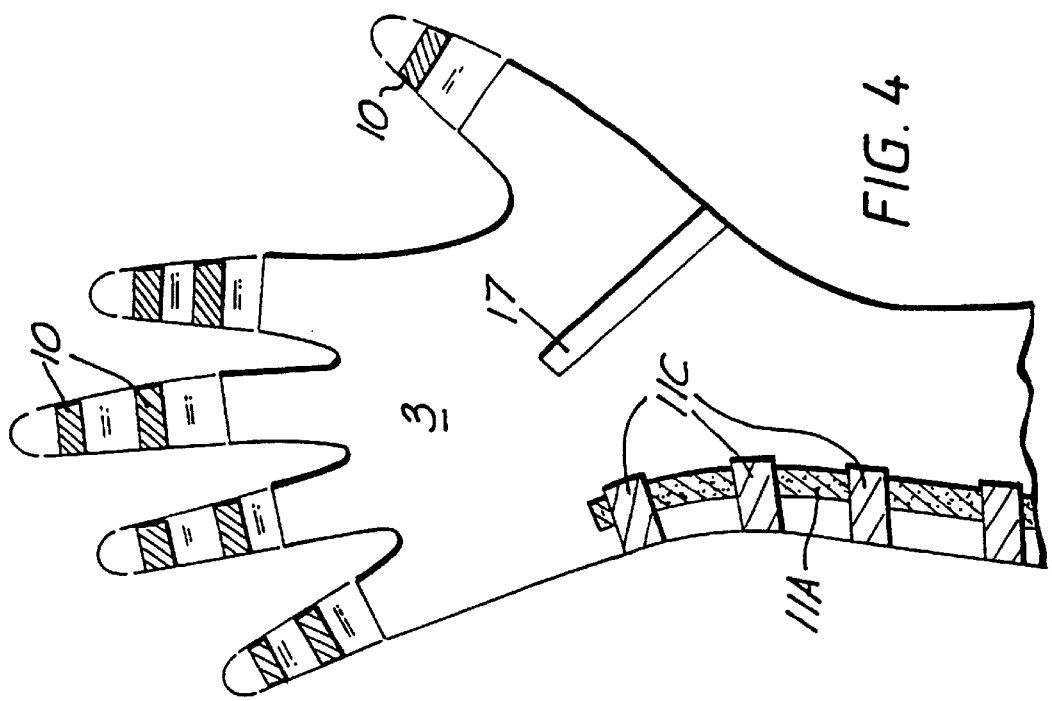
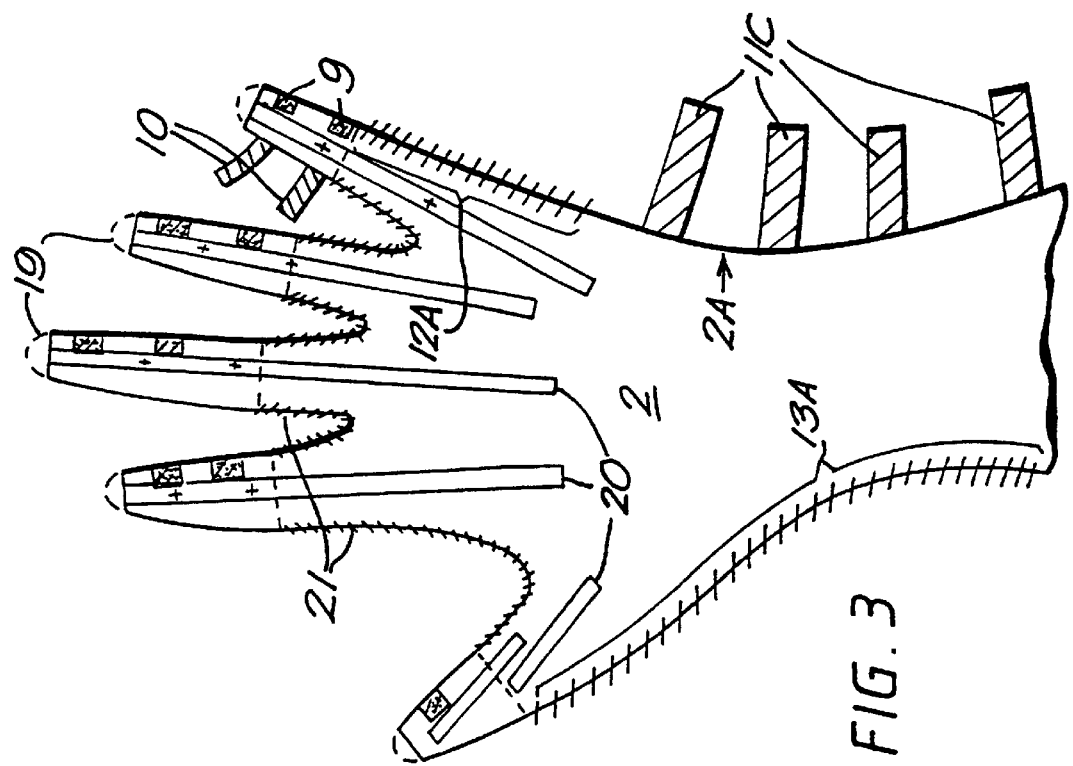

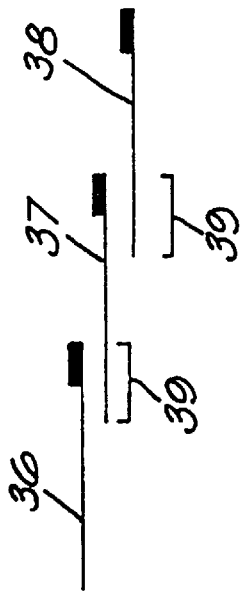
FIG. 10
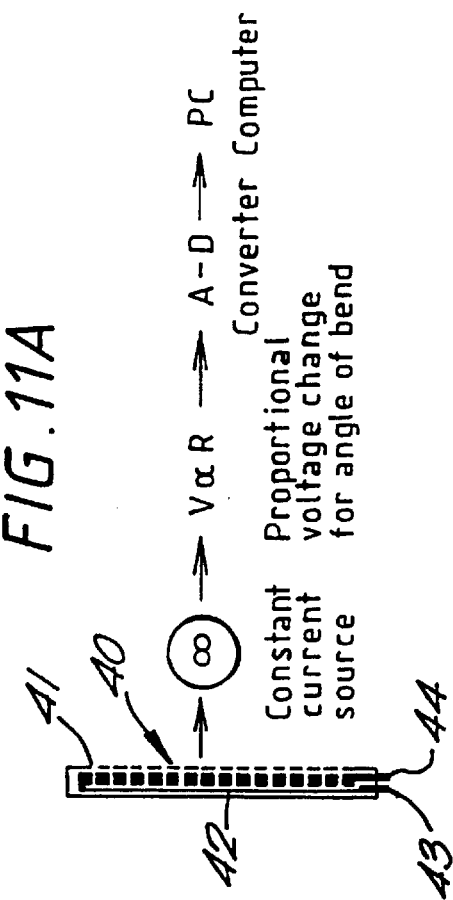
FIG. 11A
FIG. 9

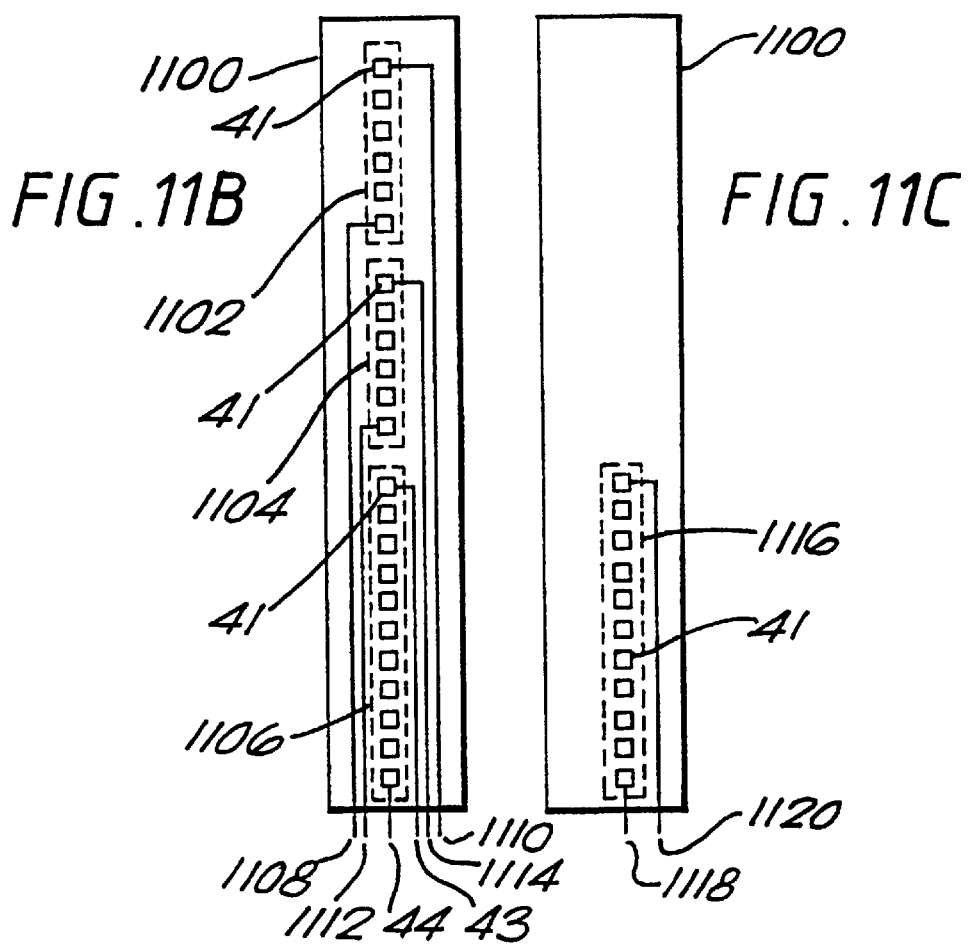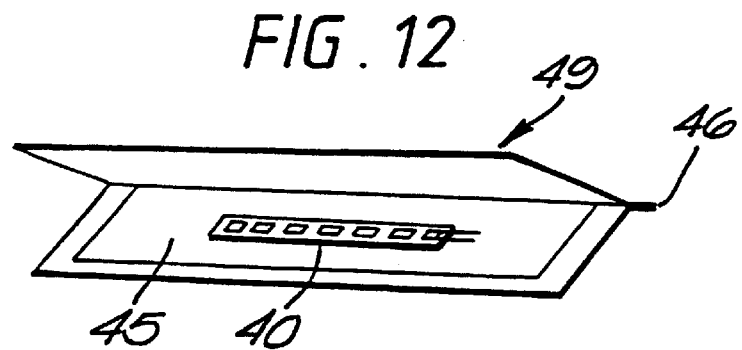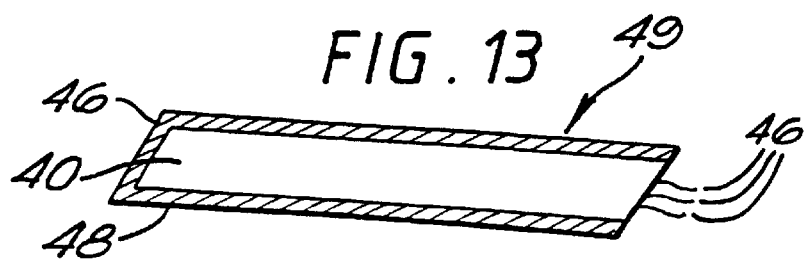

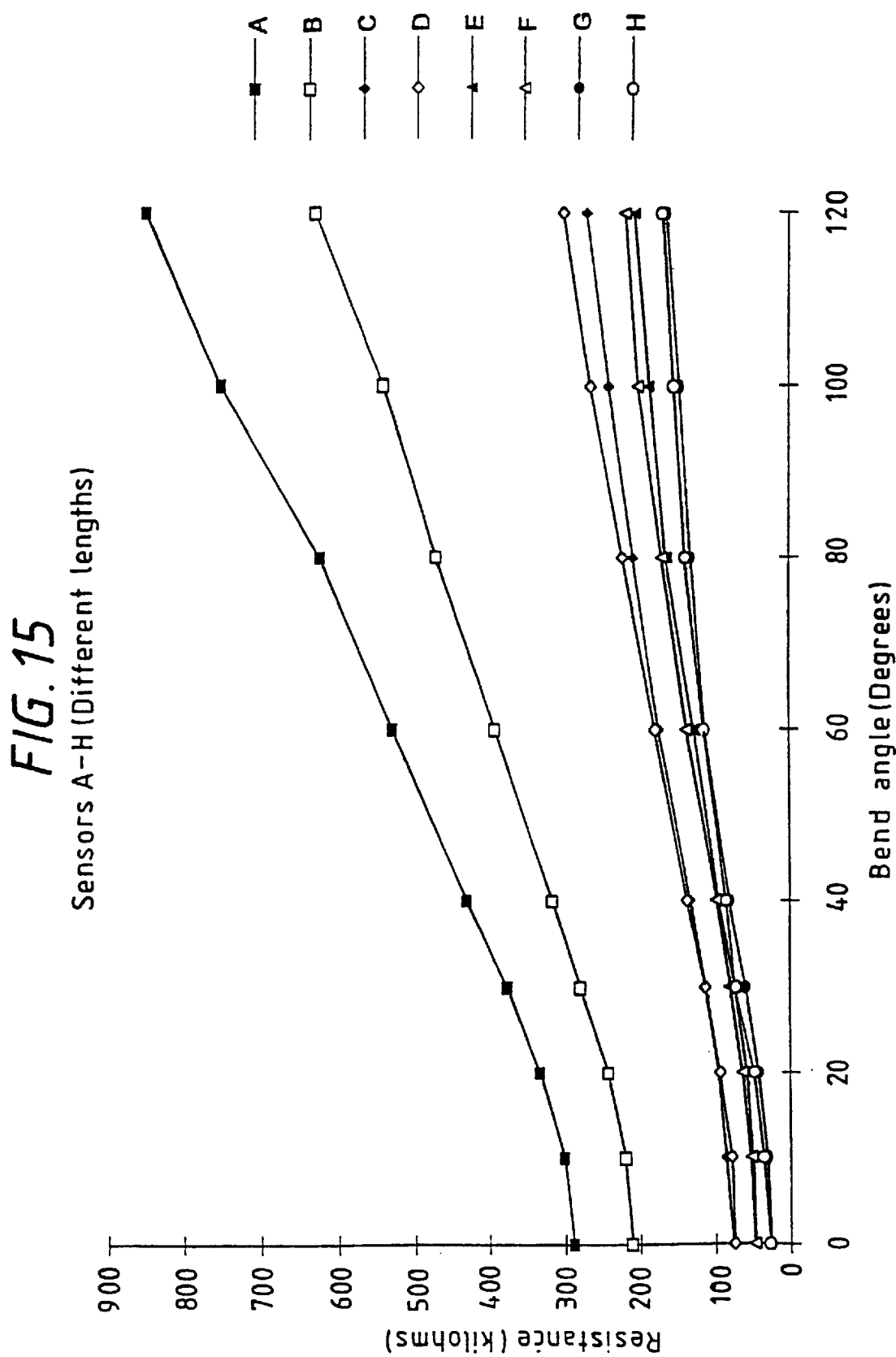

GLOVE FOR MAKING GONIOMETRIC MEASURES

This is a national phase of International Patent Application No. PCT/GB97/01382, with an international filing date of May 19, 1997, now pending.

The invention relates to a glove, and more particularly to a glove for making goniometric measurements and a method of manufacture of such a glove.

Goniometric measurements of the hand have previously been provided by a number of different gloves incorporating various sensors. An early example is a glove which uses optical flex sensors such as those detailed in U.S. Pat. No. 4,542,291. The optical sensor works on the principle that increasing the angle of bend of the sensor decreases the amount of light reaching a photosensitive detector.

The glove described in U.S. Pat. No. 4,542,291 is difficult to put on deformed, in correctly formed or temporarily misshapen hand. Furthermore, optical flex sensors are made from optical fibres, which are expensive and if damaged require replacement. Complex electronic circuitry is required to convert signals from the photosensitive detector into angular measurements.

A fibre optic instrumented elastic fabric glove has been proposed for evaluating hand function in a paper entitled "Evaluation of a Fibre Optic Glove for Semi-Automated Goniometric Measurements", Journal of Rehabilitation, Research and Development, Volume 27, no. 4, 1990, pages 411 to 424. However, this glove does not fit easily over an abnormally shaped hand or unusually sized hand. Two conversion programmes are essential to covert signals from the photosensitive detectors to useful angular measurements.

More recently, U.S. Pat. No. 5,280,265 has proposed a goniometric glove incorporating variable resistance strain sensing elements to detect complex joint movements for gesture recognition applications. This glove is aimed at utilising identified gestures to produce vocal or written symbols. Again, in deformed, or unusually sized hands, it is difficult to put on and requires complex electronics for conversion of signals from the sensors to useful angular measurements.

Providing the glove with open finger tips or a palm mesh has also been suggested for use in gripping objects or providing ventilation to the gloved hand.

Where gloves are difficult to apply to a wearer's hand, the likelihood of breakage of sensors, especially fragile sensors, and sensor connections is increased during glove application and removal. Furthermore, if a glove is not applied correctly, the sensors may not be in the appropriate position with respect to an individual's joints for reliable and accurate measurements to be made. Indeed the latter two gloves are only available in one size, thus, accurate placement of sensors with regard to different hand sizes and/or shapes is difficult.

U.S. Pat. No. 5,086,785 proposes various angular displacement sensors, such as carbon ink resistance sensors, which can be used as bend sensors affixed to a glove to determine hand position for controlling video games.

It can be seen that there is a problem with existing gloves in that they are difficult to put on, in a clinical situation in patients with temporarily or permanently misshapen hands, for example, rheumatoid arthritic hands. In some cases it is difficult to position the sensors accurately over the joints of normal hands, and this is even more of a problem with misshapen hands.

There is also a need to provide a glove for goniometric measurements which does not require complex electronics in order to output useful angular measurements.

It is therefore an object of the invention to alleviate at least some of the problems of the prior art.

It is therefore an object of the invention to alleviate at least some of the problems of the prior art.

In a first aspect, the invention provides a glove having an open aspect along at least one digit so as to facilitate application of the glove to a hand.

The glove of the invention is particularly, but not exclusively, suitable for use in the assessment of hand mobility for medical purposes, eg prior to and following surgical procedures, or for measuring the mobility of prostheses. Other applications, including virtually reality imaging and gesture recognition, are envisaged, that is, the glove may be used as an interface device for a computer.

Measurements which may be taken with the glove of the invention include angular, angular range, speed, velocity and acceleration measurements of a wearer's hand.

According to the the invention there is provided a glove used in goniometric measurements comprising a palmer having one or more finger sections and a dorsal panel having one or more corresponding finger sections the glove being characterised by:

a palmar panel having one or more finger sections extending from the base of a wearers's finger to a first point part way between the base of the finger and the distal interphalangeal joint of a wearer;

a dorsal panel having one or more corresponding finger sections extending from the base of a wearer's finger to a second point beyond the distal interphalangeal joint of the wearer; and attachment means for attaching those portions of the dorsal panel finger sections which extend beyond the palmar panel finger sections, to a wearer's finger.

In a preferred embodiment, each panel comprises four finger sections. Preferably, each panel comprises a thumb section, the palmar panel thumb section extending from the base of the thumb to a point part way between the base of the thumb and the interphalangeal joint; the dorsal panel thumb section extending from the base of the thumb to a point beyond the interphalangeal joint.

In a preferred embodiment, adjacent finger sections on one panel extend to corresponding points having regard to a wearer's finger joints.

Preferably, the attachment means are located on the dorsal panel finger sections. The attachment means may be releasable, and preferably comprises a self attaching and releasable material, for example, VELCRO loop and hook fastner. Preferably the attachment means comprises straps attached to each of the overhanging dorsal digit sections.

In a preferred embodiment, the palmar panel is permanently connected to the dorsal panel from a point adjacent to the thumb interphalangeal joint to a point adjacent to the wrist on the radial side of the glove. Alternatively, or preferably in addition, the palmar panel is permanently connected to the dorsal panel from a point adjacent to the fifth digit proximal interphalangeal joint to a third point beyond the line passing through the metacarpophalangeal (MCP) joints of the hand, on the ulnar side of the glove. Preferably the point is around 2 cm beyond the MCP line.

Preferably, the connections are permanent and are formed by stitching, gluing, heat welding or the like.

Further attachment means may be provided on the ulnar side of the glove to close the glove from around the third point to the wrist. Preferably, the further attachment means are releasable. The attachment means may comprise one or more straps having, for example, VELCRO fasteners and corresponding VELCRO panels situated on the glove.

A plurality of sensor pockets may be located about the glove. Preferably, carbon ink sensors are provided at locations about the glove.

In a further preferred embodiment, one or more sensor pockets contain first and second sensors arranged so as to measure bending in substantially opposite directions.

Preferably, one or more sensor pockets comprises two or more sensors arranged to measure bending of different joints. One pocket per finger containing two, or preferably three sensors, may be provided. The sensors in each pocket may overlap. A layer of insulating material may be placed beneath the or each sensor within a pocket for electrical safety. Prior to insertion into a pocket, the sensors are sprayed with a non-conducting coating such as Conformat acrylic coating RS 714462 for electrical safety. The sensor/wire contact area is reinforced with silicone sealant or the like.

In a further preferred embodiment, there is provided a goniometric measurement system comprising a glove as herein described and an electronic processing unit, preferably comprising at least one constant current source and preferably one per sensor. Preferably, one or more calibration curves are also provided.

The glove comprises a palmar panel with finger sections extending short of the distal interphalangeal joint and preferably proximal to the proximal interphalangeal joint of a wearer, and a dorsal panel having finger sections extending to almost the tip of the finger of the wearer and attachment means to strap the overhang to the wearer's fingers.

In a further preferred embodiment there is provided a method of constructing a glove for goniometric measurements comprising the steps of:

providing palmar and dorsal panels as herein described;

placing the palmar and dorsal panels about the hand;

affixing sensors, and preferably sensor pockets containing sensors, to the panels at appropriate locations adjacent to the joints of the hand.

Preferably, the method comprises the further steps of:

removing the glove; and, permanently affixing the sensors, or sensor pockets containing sensors, to the glove.

Preferred embodiments of the invention will now be described by way of example only, with reference to the accompanying Drawings in which:

FIG. 1 illustrates a plan view of a dorsal panel for a glove in accordance with the invention;

FIG. 2 illustrates a plan view of a palmar panel corresponding to the panel shown in FIG. 1;

FIG. 3 illustrates a plan view of a dorsal panel of a further embodiment of a glove showing a further arrangement of VELCRO attachment straps and also illustrating the position of stitching;

FIG. 4 illustrates the plan view of a palmar panel corresponding to the panel in FIG. 3, also showing the positioning of attachment straps around the fingers and thumb;

FIG. 9 is a plan view of a dorsal panel illustrating a sensor pocket for a finger and three sensors therein;

FIG. 10 illustrates the overlap of the three sensors illustrated in FIG. 9;

FIG. 11A is a plan view of a carbon ink sensor;

FIGS. 11B and 11C show dorsal and palmar views of a further carbon ink sensor.

FIG. 12 is a schematic perspective view of a sensor pocket containing a carbon ink sensor prior to closure;

FIG. 13 is a schematic perspective view of a closed sensor pocket;

FIG. 15 illustrates a set of calibration curves for sensors A–H, A being the longest and H the shortest.

Figure 6:
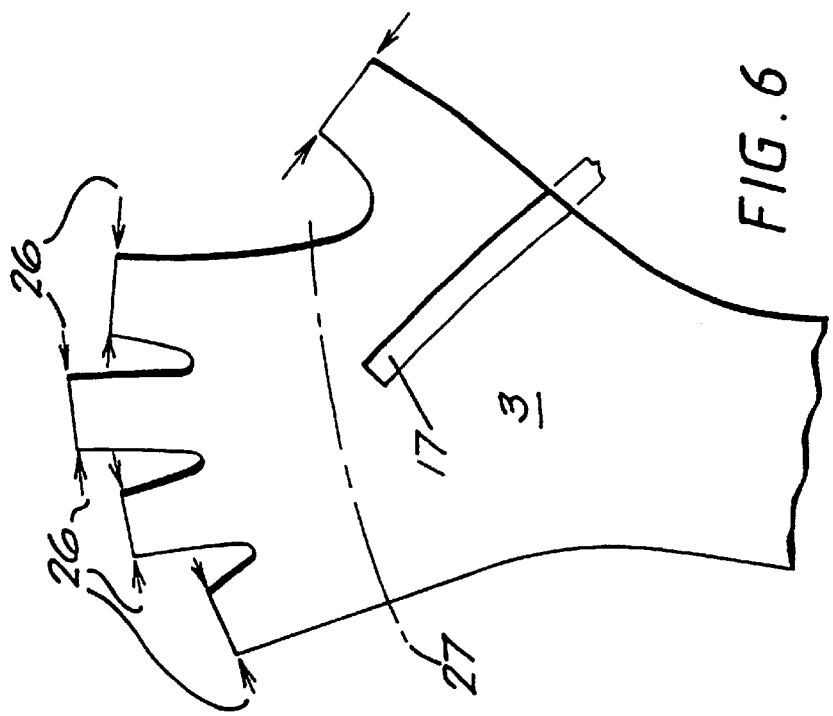
FIG. 6 illustrates a plan view of a palmar panel, showing the positions of various joints and a palmar sensor.

Referring now to FIG. 1, dorsal panel 2 comprises four finger sections and one thumb section, which sections are sized to extend beyond the distal interphalangeal (DIP) and proximal interphalangeal (IP) joints 4, 6 of the fingers and thumb respectively. The proximal interphalangeal (PIP) joints are indicated at 5. The ends of the wearer's digits are indicated at 19.

The dorsal panel, when worn, completely covers the back of the hand and the metacarpophalangeal joint axes 7. Panel 2 is composed of flexible lycra.

A corresponding palmar panel 3 is shown in FIG. 2. The finger, and thumb, sections of panel 3 do not extend as far along the finger, and thumb, as the corresponding sections of panel 2. Typically, the palmar finger and thumb sections extend only as far as the proximal interphalangeal joint 5 or interphalangeal joint 6 respectively. The extent of the palmar panel digit sections along the fingers and thumb is indicated in FIG. 1 at dotted line 18.

Panels 2 and 3 are sewn together along the ulnar and radial seams at 12A, 12B and 13A, 13B. The dorsal panel finger sections are strapped to fingers 19 by means of VELCRO panels 9 and straps 10. Similarly, the main portion of panels 2 and 3 are releasably fixed together following insertion of the hand by use of velcro panels 11A, 11B and straps 11C.

The end portion of the distal phalanges of a wearer's digits extend, as shown in, for example, FIG. 3, beyond the end of the corresponding dorsal panel finger sections. However, an alternative embodiment of employs caps for receiving respective ends of the distal phalanges. The caps can be realised as, for example, substantially U-shaped arcuate members attached to and extending from the dorsal panel finger section. Alternatively, the finger section of the glove may be designed so as to retain or provide a conventional glove tip whilst having an open aspect at the palmar side of the fingers sections of the glove. A still further embodiment may provide a thimble-like members for securely receiving the tips of the distal phalanges of a wearer's digits.

Figure 7:
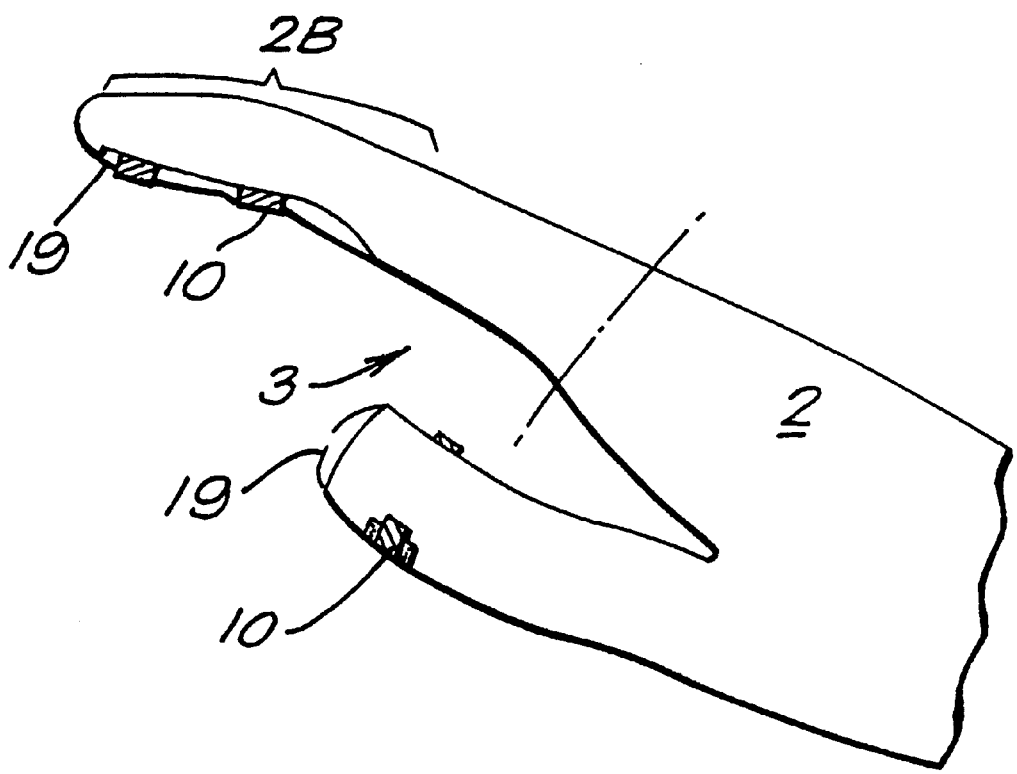
FIG. 7 illustrates a side view of a glove when positioned on a hand.

The provision of distal phalanx receiving portions to the glove advantageously reduces or obviates relative linear movement between the material of the glove and the wearer's hand. Reducing or obviating any such movement ensures that the sensors are substantially correctly positioned relative to the Joints during use of the glove. Such a distal phalanx receiving portion is illustrated in FIG. 7. The portion receiving the tip of the distal phalanx and ensures that sensor position at 2B maintains a substantially constant position relative to the underlying finger.

Various sensors are illustrated in FIGS. 1 and 2. In particular, gusset sensors 14 for measuring abduction of the fingers and thumb are shown. Ulnar deviation sensors are shown at 16A and 16B. Sensor 16A extends from the PIPJ of the index finger to a point around 2 cm proximal to the MCPJ of the index finger. Palmar abduction of the thumb is measured by palmar sensor 17. Wrist sensors 15 are responsive to bending of the wrist.

Differently sized gloves such as hand sizes 7, 7½, and 8 can be used to facilitate accurate placement of sensors with regard to joints.

In the following Figures, like reference numerals refer to aforementioned like referenced features.

Referring to FIG. 3, dorsal panel 2 is illustrated indicating stitched regions 21 between the fingers. The stitched areas 21 extend from the IP joint of the thumb to the PIP joint of the index finger and from the PIP joint of the index finger to the PIP joint of the middle finger and so on.

Releasable fasteners in the form of VELCRO panels 9 having hooks and straps 10 comprising VELCRO eyes are shown. Two fasteners are provided per finger, one between the PIP and the DIP joints and one beyond the DIP joint of each finger, in order to position and secure the finger sections of the dorsal panel to the finger during measurements. Thus, straps 10 are situated at the mid point of the middle and distal phalanges of the fingers and at the mid point of the distal phalanx of the thumb.

An opening 2A is provided in the glove when fully sewn to allow a wearer's hand to be easily inserted. Straps 11C are provided to ensure that the glove remains securely fitted to a wearer's hand during use. This is more clearly shown in FIG. 4 wherein straps 11C are seen attached to a VELCRO fastener 11A.

Figure 5:
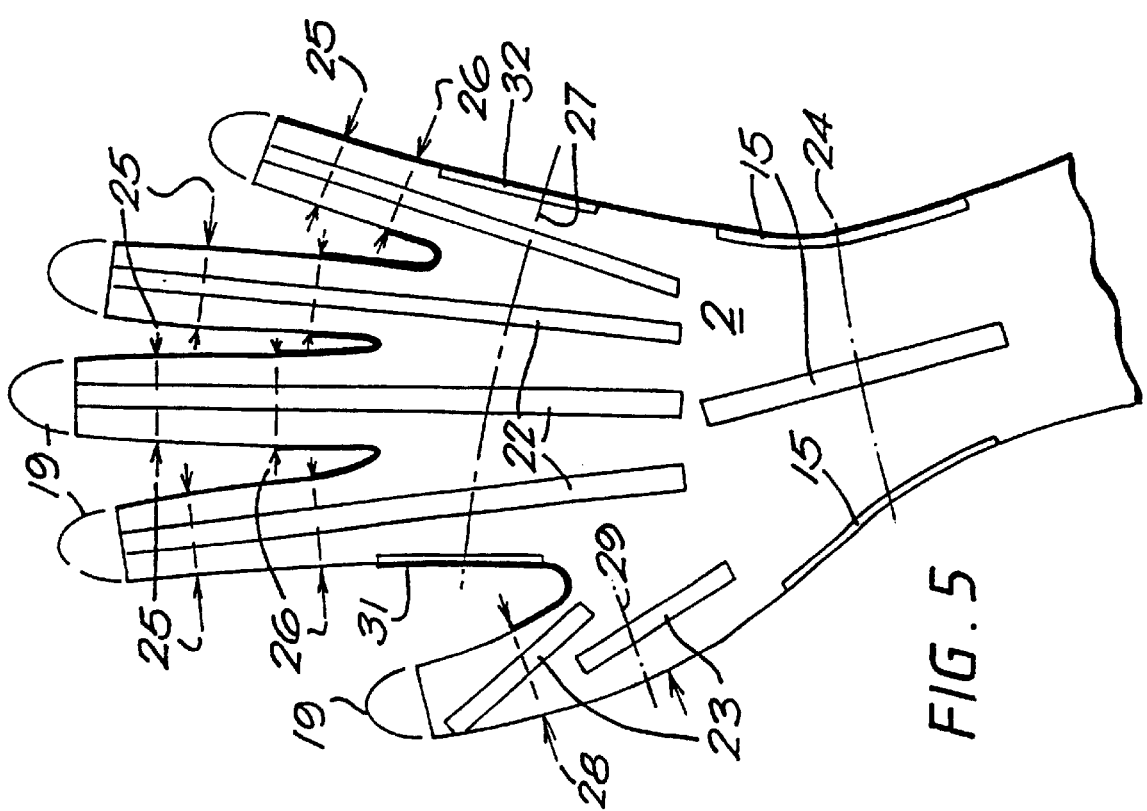
FIG. 5 illustrates the plan view of a dorsal panel, showing the locations of various joints and sensors.

Referring now to FIGS. 5 and 6, there is shown a dorsal aspect of the glove. The locations of the DIP, PIP and metacarpophalangeal (MCP) joints of the fingers, 25, 26 and 27 respectively, and the IP and MCP joints of the thumb, 28 and 29 respectively, are indicated.

The locations of the sensors are based around the anatomical landmarks of the hand, ie the distal interphalangeal joints (DIPJ), the proximal interphalangeal joints (PIPJ), the metacarpophalangeal joints (MCPJ) and the wrist joint. The sensors are received in appropriately shaped pockets 22, 23, 15, 32 and 14.

Finger sensor pockets 22, covering the DIP, PIP and MCP joints, are provided along the midline of each ray. Thumb IPJ and MCPJ sensor pockets 23 are disposed obliquely across the joints so as to position the sensors over the joints.

Finger deviation sensors 31 and 32 are positioned on the radial and ulnar sides of the glove respectively. On the radial side, the deviation sensor 32 extends from approximately 5 mm short of the PIP joint of the fifth digit to within around 15 mm of the MCP joint of the fifth digit. On the ulnar side, the finger deviation sensor extends from around 5 mm short of the PIPJ of the second digit to around 15 mm proximal to the MCPJ of the second digit.

Finger abduction sensors 14 are positioned in the saddle areas between the fingers and thumbs. Sensor pockets for sensors 14 are sewn to the glove adjacent stitched regions 21 (not shown). The finger abduction sensors, alternatively known as web sensors, 14 extend from the PIPJ of one finger to the PIPJ of the neighbouring finger for fingers 2 to 4 and from the IPJ of the thumb to the MCP of the index finger.

Four wrist sensors 15 are provided about the wrist to measure flexion, extension and abduction/adduction.

Each sensor is placed over each joint so that the mid point of the sensor overlies the axis of the joint when fingers and thumb are extended.

Referring now to FIG. 6, the palmar sensor pocket 17 for measuring thumb abduction is located at the midpoint of the thumb metacarpal and falls just short of the metacarpal head of digit III.

Typical sensor lengths for a small glove (small, medium and large gloves are provided) are as shown in Table 1:

TABLE 1

| Joint | Sensor Position | | | | | Total length of chain of sensors |
|---|---|---|---|---|---|---|
|  | MCP | Overlap | PIP | Overlap | DIP |  |
| Index | 62 | 12 | 53 | 20 | 42 | 126 |
| Middle | 58 | 6 | 53 | 13 | 45 | 138 |
| Ring | 58 | 10 | 50 | 14 | 40 | 131 |
| Little | 50 | 18 | 44 | 8 | 40 | 105 |

The lengths of the other sensors are as follows: palmar sensor 53 mm, thumb PIP sensor 62 mm, thumb MCP sensor 48 mm, wrist midline sensor 80 mm, wrist radial sensor 56 mm, wrist ulnar sensor 82 mm, finger deviation sensors 40 mm on the ulnar and radial sides, finger abduction sensors, for web space 1 between the finger and thumb 53 mm, for web space 2 between the second and third digit 52 mm, for web space 3 between the third and fourth digits 49 mm, and for web space 4 between the fourth and fifth digits 45 mm.

Referring now to FIG. 7, there is shown a side view of a glove positioned about a user's hand illustrating straps 10 and the user's fingers and thumb 19. As can be seen from the Figure, the glove provides a close fit about the fingers and thumbs. This is the case, even where a wearer's fingers are misshaped or in correctly formed, or deformed as dorsal digit extensions 2B may be more closely and more accurately positioned using straps 10.

Figure 8:
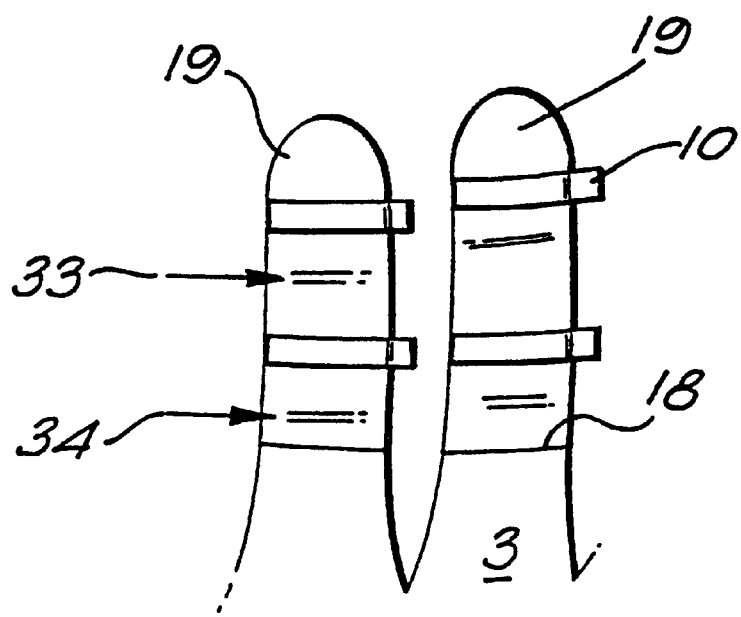
FIG. 8 illustrates a plan view of two fingers seen from the palmar side illustrating the position of the palmar panel and fixing straps.

FIG. 8 illustrates the position of straps 10 with regard to the distal joint and proximal joint creases 33 and 34 of the fingers 19. The limit of the glove palmar surface is illustrated at 18. Straps 10 hold the dorsal surface of the glove close to the hand at the mid-point of the middle and distal phalanges.

The arrangement of particular sensors within a given sensor pocket for a digit is illustrated in FIG. 9. Here sensors 36, 37 and 38 are positioned above the DIP, PIP and MCP joints respectively. The sensors overlap at regions 39. The extent of the overlap for each digit is given in TABLE 1. In addition, sensor 38 comprises two portions 38A and 38B. The portions 38A and 38B have been formed from a single carbon ink sensor which has been cut along its length and one portion reversed with respect to the other in order to measure the MCP joint in opposing angular directions. An insulating layer formed from quick setting insulating gel is placed between 38A and 38B.

FIG. 10 illustrates more clearly the regions of overlap 39 between sensors 36, 37 and 38.

FIG. 11 illustrates an example of a carbon ink sensor 40 having pads 41, metallic strips 42 and connecting stubs 43 and 44. Where the stubs 43 and 44 join the sensor, this area is reinforced with a silicone sealant, or the like. The arrangement of the sensor within a pocket is illustrated in FIGS. 12 and 13. Here, sensor 40 is placed within pocket 49 which is made from flexible lycra. The sensor is placed above an insulating layer 45 in order to reduce the risk of electric current leakage to a wearer.

A 2 mm flange is stitched around the sensor/pocket arrangement. This is particularly useful for further stitching of the pocket to the glove. Thus the stitch area 48 provides a border around sensor area 40. The stitches are placed close to the sensor so that the sensor, or sensors, fit snugly and are relatively securely held within the pocket. Wires 46, connectable to the stubs 43 and 44, are passed to a circuit such as that illustrated in FIG. 14.

Although the above embodiment uses a plurality of separately formed sensors which combination are used to monitor the flexibility of the distal interphalangeal joint, proximal interphalangeal joint and the metacarpophalangeal joint respectively, the present invention is not limited thereto and an embodiment can be realised in which a single flexible strip, for example plastic, bears a plurality of carbon pads arranged into a plurality of groups. Each group of carbon pads has corresponding electrical connections thereto. Each group of carbon pads is arranged so as to be actuable by a corresponding phalangeal joint.

Referring to FIG. 11B, there is shown a sensor 1100 comprising first 1102, second 1104 and third 1106 groups of linearly disposed carbon pads. Each group of carbon pads has corresponding electrical terminals associated therewith 43, 44, 1108 to 1114.

The carbon pads 41 within each of the first, second and third groups are linearly disposed relative to one another. Each group of carbon pads operates in a substantially identical manner to the separate sensors 36, 37 and 38 described above when the first, second and third portions are disposed so as to be actuable by the distal interphalangeal joint, the proximal interphalangeal joint and the metacarpophalangeal joints respectively.

With reference to FIG. 11B, there is shown a view of a sensor, viewed from the dorsal side, for use in monitoring the mobility of the digits of a hand.

Referring to FIG. 11C, there is shown the sensor 1100 viewed from the palmar side for use in monitoring the mobility of the metacarpophalangeal joint. This reversed side of the sensor 1100 comprises a portion 1116 of linearly disposed carbon pads 41, together with corresponding electrical contacts thereto 1118 to 1120. This fourth portion 1116 of carbon contact pads is arranged to measure the degree of hyperextension of the metacarpophalangeal joint. It will be appreciated that the third 1106 and fourth 1116 portions of the sensor 1100 are functionally equivalent to the above sensors 38a and 38b.

Preferably, the third 1106 and fourth 1116 portions are arranged to be substantially coplanar and facing in mutually opposite directions.

The advantages associated with having metacarpophalangeal joint sensors for monitoring both flexion and hyperextension disposed in a substantially coplanar manner on opposite sides of a strip of plastic are that, firstly, the tendency of portions 38a and 38b of the above embodiments to separate upon flexion of the metacarpophalangeal joint is eliminated and, secondly, the total surface area required by the sensor for monitoring the hyperextension and flexion of the metacarpophalangeal joint is substantially reduced.

Although the sensor 1100 above has the third 1106 and fourth 1116 portions disposed on opposite sides of a single plastic strip, the present invention is not limited thereto. An embodiment could equally well be realised in which the first 1102, second 1104 and third 1106 portions are disposed on one plastic strip while the fourth portion 1116 is disposed on a separate plastic strip. The separate plastic strips would then be disposed such that the third 1106 and fourth 1116 portions are positioned substantially coplanarly relative to one another and arranged to face in mutually opposing directions.

Figure 14:
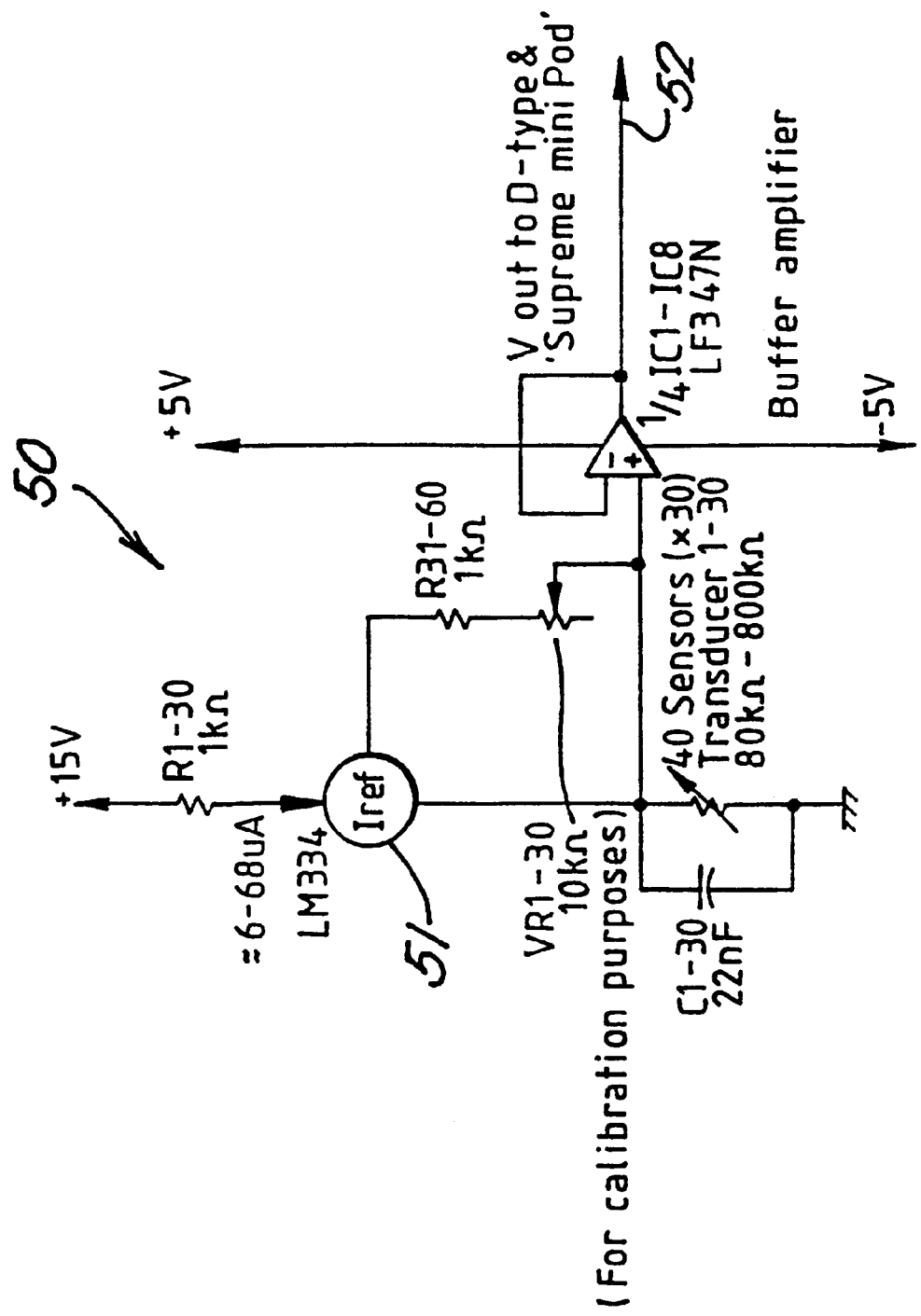
FIG. 14 illustrates a circuit containing a constant current source, for converting the signals from the carbon ink sensors to signals suitable for a computer.

In FIG. 14, the circuit 50 comprises a constant current source 51 arranged to power variable resistance sensors 40 so as to provide an output 52 voltage signal. The voltage signal 52 is suitably supplied to an A/D converter of means for processing the digital output of said A/D converter, for example, a suitably programmed computer. For each sensor, a corresponding circuit 50 as illustrated in FIG. 14 is provided.

The output signal 52 of each circuit is proportional to the change in resistance of an associated sensor. The arrangement provides a voltage change which is proportional to the change in resistance of the sensor. Since the resistance of carbon ink sensors is substantially proportional to the angle of bend, that is, to the extent to which the sensor is flexed, the change in voltage gives a measurement which is directly proportional to the angle of bend. Typical calibration curves are illustrated in FIG. 15 which allow the resistance of the sensor (or the output voltage) to be translated into a corresponding indication of the degree to which the sensor has been flexed. The A/D converter provides a suitable interface to a computer. Custom software is designed for use with the glove. The software is written in C++. The software is arranged to give effect to the mapping between the output voltage and the angle of bend.

Examples of how to make the glove will now be described.

EXAMPLE 1

The first glove manufactured consisted of three pieces of Lycra material grade Lycra Soft Shine 25444 from Spentex BCA, England, cut to the size of an individual's hand.

A pattern of the hand is drawn by placing the right hand of the individual onto a piece of paper with the fingers and thumb extended and abducted. Dorsal Panel 2 is made with a border of 0.5 cm width around the drawn hand shape. The positions of the small joints of the hand and wrist are marked. Thirty sensors are placed between two of the layers of lycra at locations corresponding to the small joints of the hand as well as the wrist. The locations and numbers of the sensors are shown in Tables 2, 3, 4 and 5 as follows:

TABLE 2

| | FINGERS |
|---|---|
| No. | LOCATION |
| 4 | DIPJ Distal interphalangeal |
| 4 | PIPJ Proximal interphalangeal |
| 8 | MCPJ Metacarpophalangeal |

TABLE 3

| | THUMB |
|---|---|
| No. | LOCATION |
| 2 | IPJ Interphalangeal |
| 1 | MCPJ Metacarpophalangeal |
| 2 | CMC Carpometacarpal |

TABLE 4

| | WRIST |
|---|---|
| No. | LOCATION |
| 2 | Abduction/Adduction |
| 2 | Flexion/Extension |

TABLE 5

INTERPHALANGEAL/ABDUCTION/ADDUCTION

| No. | LOCATION |
|---|---|
| 4 | (gusset sensors) |
| 1 | Palmar Abduction Thumb |

For the fingers, sensors 36, 37 and 38 are placed on one of the pieces of Lycra with the midpoint of each sensor for a given joint being disposed over the corresponding marked joint position. Each sensor is cut to an appropriate length and the circuit re-established with an electroconductive paint. This is done so that only one sensor crosses a given joint, that is to say, any given sensor is actuated by a single corresponding joint.

The metacarpophalangeal joints of the fingers are able to hyperextend. Therefore, in order to identify the amount of hyperextension as well as the flexion of any one of these joints, two sensors 38A and 38B are cut longitudinally (leaving the metallic contact ends intact), one sensor is inverted and glued to the other at the contact ends and a piece of insulating malleable plastic is disposed between the metallic contacts to prevent short circuits therebetween. This will allow both flexion and hyperextension of the metacarpophalangeal joints to be recorded.

A similar method is applied to the IP and CMC joints of the thumb as well as the wrist. Thus, at those joints which are capable of hyperextension and flexion, such sensors comprising two portions are used.

The sensors are then replaced on the piece of Lycra at the midpoint of each digit, and tacked into place with cotton. Wires are then soldered onto the stubs of each sensor and the colour code of the wire connected to a given sensor is recorded. Once the fingers sensors are soldered and tacked into place, a second piece of Lycra is placed over the first and a run of stitches is placed along either side of each series of sensors to hold them in place laterally. A similar method of affixing the sensors is employed for the thumb.

Separate Lycra pockets are constructed for each sensor of the wrist, palm and the interdigital abduction-adduction sensors. Each pocket for the wrist region is then sewn onto the first piece of Lycra in the appropriate marked positions and the corresponding sensor is soldered to wires, inserted into the pocket and the pocket closed with sutures.

Gussets of 2.0 cm in width are cut from the same piece of lycra and sewn to each finger and thumb in web spaces I–IV, which gussets also serve to suture the two pieces of Lycra together along each digit. The pockets for the abduction sensors are then sutured to each gusset in the region between the IP joint of the thumb and the MCP joint of the index finger and in the region between the PIP joints of each of the fingers II–V.

Abduction sensors are then incorporated into each gusset pocket and the appropriate wires soldered to each sensor after threading the wires between the two pieces of Lycra over each digit exiting opposite the PIP joints for the fingers and opposite the MCP joint of the finger for the 1st web abductor sensor. The pockets are then sealed with cotton.

The thumb palmar sensor pocket is sutured to the third piece of Lycra in an oblique plane at the midpoint of the palm level and middle finger MCP joint to the midpoint of the first metacarpal. The third palmar piece of Lycra is sewn to the dorsal pieces with the sensors in situ. The suturing is limited to only completing the fingers and thumb at this point. The thumb palmar abduction sensor is then placed into its corresponding pocket and the wires soldered in place and reinforced. The earth wires of each sensor are then connected together between the two pieces of dorsal Lycra and soldered to four earths returning from the glove to the amplifier circuit via a 36 way cable. The suturing of the three layers of Lycra is then completed on the radial side of the glove.

The two dorsal layers of Lycra on the ulnar side of the glove are sutured together, but the palmar piece is left free. VELCRO strapping hooks and eyes are applied between the palmar piece of Lycra and the dorsal sensor pieces which allows an opening or open aspect for ease of fitting of the glove to an individual.

EXAMPLE 2

In the glove of Example 1, the sensors incorporated along each ray are linearly disposed. However, upon digit flexion, the position of the MCP sensors is not directly over the MCP joint, but to one side. This is due to the angulation which the articulated chain of phalanges make with their corresponding metacarpals in flexion.

The thumb sensors have similar positioning problems when their locations are taken from the marked pattern, the MCP joint sensor being too far towards the ulnar.

In order to improve the ease of fitting, therefore, a lighter, more pliable, grade of Lycra is used; Lycra 25034 Power Net from Spentex BCA Limited.

Firstly, the basic glove is made. The glove shape is traced and cut out of two pieces of Lycra in the appropriate glove size. Gussets of 2 cm are stitched to the dorsal piece, incorporating pockets for the web sensors 14 running between the IP joints of the fingers in webs II, III and IV, and from the IP joint of the thumb to the MCP joint of the index finger in web I. The palmar aspect of the glove is then temporarily stitched into place, allowing the glove to be worn.

To improve digit sensor position for measurement and glove safety, digit sensors are placed in four Lycra pockets with an insulation layer between the sensors and the wearer. Four strips of Lycra 14 cm in length and 2 cm wide, are folded in half longitudinally with a piece of flexible insulating plastic in between, and then stitched along the folded side, leaving a 2 mm flange for subsequent stitching to the glove. The sensors are then cut to the appropriate lengths and placed in the pockets via the open side, so that the midpoint of each sensor overlays the appropriate joint. For finger sensors 36, 37 and 38, a slight overlap 39 is allowed between the distal aspect of one sensor and the proximal part of another sensor. The area of overlap is insulated with fast setting silicone rubber compound, for example, R.S. components number 555–588. Wires are then soldered to each sensor and fast setting silicone rubber compound is also applied around these contacts for insulation and to provide support for the soldered wires.

The pockets are then completed by stitching the open side tightly up to the side of the sensor and closing the distal end of the pocket. The proximal end of the pocket is left open for the passage of the sensor wires. The completed pockets have a 2 mm flange all around.

The glove is worn and the pocket/sensor complex placed along each ray in the appropriate position and tacked into place. The palmar side of the glove which was attached temporarily is then removed and the pockets formally stitched into place to hold the Lycra sensor pocket strip in the correct position on the dorsal surface of the glove.

Similarly, for the sensor/pocket combinations on the thumb, wrist, palm and ulnar deviation sensors for the fingers.

Once all of the sensors have been positioned and stitched, the palmar surface of the glove is addressed. Problems are encountered with the fingers being a very tight fit and hence difficult to apply. To provide a glove which, though close fitting, is not difficult to apply the palmar aspect of the fingers is left open, and the dorsal aspect of the glove is closely applied to the hand by small VELCRO straps.

The palmar aspect of the glove is therefore completed on the radial side from the IP joint of the thumb to the wrist, and the ulnar side completed from the PIP joint of the little finger to the distal palmar crease. Like the first glove design, the majority of the ulnar border of the glove is left open for ease of application with VELCRO fasteners to complete the glove on wearing. The web spaces between the palmar and dorsal surfaces of the glove are closed along the line of the abduction sensor pockets, leaving the palmar surfaces of the fingers open from the PIP joint and from the IP joint of the thumb distally.

To neaten the dorsal appearance of the glove and to hide the multitude of wires, a further piece of Lycra is cut to the same size as the dorsal piece and stitched to the dorsal surface of the glove. The number and locations of the sensors are as follows:

| No. | LOCATION |
|---|---|
| | FINGERS |
| 4 | DIPJ Distal interphalangeal |
| 4 | PIPJ Proximal interphalangeal |
| 8 | MCPJ Metacarpophalangeal |
| | THUMB |
| 2 | IPJ Interphalangeal |
| 1 | MCPJ Metacarpophalangeal |
| 2 | Finger Deviation Sensors |
| | WRIST |
| 2 | Abduction/Adduction |
| 2 | Flexion/Extension |
| INTERPHALANGEAL/ABDUCTION/ADDUCTION | |
| 4 | (gusset sensors) |
| 1 | Palmar Abduction Thumb |

| | Small glove: | |
|---|---|---|
| Sensor Position | Approximate length (mm) | |
| Web Space I | 52 | |
| Web Space II | 48 | |
| Web Space III | 45 | |
| Web Space IV | 51 | |
| Palm | 54 | |
| | Ulnar | Radial |
| Finger Deviation | 48 | 52 |
| Thumb PIP | 52 | |
| Thumb MCP | 50 | |
| Wrist Radial | 56 | |
| Wrist Ulnar | 80 | |
| Wrist Midline | 80 | |

Referring to FIGS. 11A to 11C, in particular FIG. 11A, the carbon ink bend sensor 40 consists of a thin strip of malleable plastic 100 mm by 6 mm in size. Carbon is sprayed and fixed onto one side of the plastic strip forming a track 3 mm wide. Electroconductive paint is applied over this track to form a series of forty contact pads connected to a metal stub or terminal 44 at one end. Conductive paint 42 is also applied to the opposite end of the track from the metal terminal contact pad and brought back to the metal terminal end to one side of the carbon track/contact pads complex. Here another metal terminal or stub 43 is connected to the conductive paint track. Hence a circuit is formed between the two metal terminals.

As the plastic strip is bent, the carbon molecules between the contact pads move apart causing a change in resistance.

The sensor can be shortened simply by trimming the end furthest from the metal terminals 43 and 44, and applying electroconductive paint between the conductive paint strip and the carbon track/contact pads arrangement to complete a circuit. Similarly the sensor may be cut longitudinally to allow for greater flexibility of the plastic strip, see sensors 38A and 38B. Again, electroconductive paint should be applied between the paint track and the carbon track/contact pads to complete the circuit after cutting.

The sensors underwent a series of assessments to determine their characteristics. After shortening of the sensors it is possible to get consistent almost parallel gradient curves, as seen in FIG. 15. For a given length carbon ink bend sensor, given the original resistance and the gradient of the curve, the bend angle for a given resistance can be calculated.

Referring now to FIG. 14, N constant current circuits 50, where N is the total number of sensors, are used to feed each sensor 40 incorporated into the glove from a reference current 51. By Ohms law (V=IR), the constant current source allows a proportional voltage to be developed across each sensor as the resistance of the sensor changes during flexing of the sensor. This proportional variation of voltage for a given angle of bend is then converted into a digital format via an A/D converter (not shown). The A/D convertor is incorporated into the design of an amplification unit and the digital output fed into a computer (not shown) via a parallel printer port. Alternatively, the computer may comprise an A/D converter. In such a case, the output signal of the buffer is fed directly into the computer's A/D converter.

Although the above embodiment utilises a parallel printer port to transfer data to the computer for subsequent processing, the present invention is not limited thereto. The data produced from the A/D converter could equally well be transferred to the computer via a serial port using a parallel-to-serial converter.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or stens are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A glove used in goniometric measurements comprising:

a palmar panel having one or more palmar finger section: extending from a base of a wearer's finger to a first point part way between the base of the finger and a distal interphalangeal joint of the wearer;

a dorsal panel having one or more dorsal finger section corresponding to the palmer finger section, the dorsal finger section extending from the base of the wearer's finger to a second point beyond the distal interphalangeal joint of the wearer, a portion of the dorsal finger section extending beyond the palmer finger section; and attachment means for attaching the portion of the dorsal finger section which extends beyond the palmar finger section, to the wearer's finger.

2. A glove according to claim 1, in which, the or each palmar panel finger section extends to a point proximal to the proximal interphalangeal joint.

3. A glove according to claim 1, in which the dorsal panel finger sections extend to a point adjacent the tip of the finger.

4. A glove according to claim 1, in which each panel comprises four finger sections.

5. A glove according to claim 1, in which each panel comprises a thumb section, the palmar panel thumb section extending from the base of the thumb to a point part way between the base and the interphalangeal joint of the thumb and the dorsal panel thumb section extending from the base of the thumb to a point beyond the interphalangeal joint of the thumb.

6. A glove according to claim 1, in which each one of the finger sections on the dorsal panel extends to a point corresponding to an interphalangeal joint location on a wearer's finger.

7. A glove according to claim 1, in which the attachment means are located on the dorsal panel digit sections.

8. A glove according to claim 1, in which the attachment means are releasable.

9. A glove according to claim 1 in which the attachment means comprises one or more straps per digit.

10. A glove according to claim 7, in which the attachment means comprises VELCRO loop and hook fasteners.

11. A glove according to claim 1, in which the palmar panel has a radial side that is permanently affixed to the dorsal panel along an edge of said glove from a point adjacent to the thumb interphalangeal joint to a point on the wrist on a radial side of the glove.

12. A glove according to claim 1, in which the palmar panel is permanently affixed to the dorsal panel along an ulnar side edge of said glove from a point adjacent to the fifth digit proximal interphalangeal joint to a point substantially 2 cm proximal to the metacarpophalangeal joint line on the ulnar side of the glove.

13. A glove according to claim 11, in which the radial side of the palmar panel is permanently affixed to the dorsal panel by stitching, gluing, or heat welding.

14. A glove according to claim 1, in which further attachment means are provided on the ulnar side of the glove from a point substantially 2 cm proximal to the metacarpophalangeal joint line to a point adjacent to the wrist.

15. A glove according to claim 14, in which the further attachment means are releasable.

16. A glove according to claim 14, in which the attachment means comprises one or more straps.

17. A glove according to claim 14, in which the attachment means comprises VELCRO loop and hook fastners.

18. A glove as claimed in claim 1, further comprising one or more sensors disposed on said glove, said sensors being arranged to be actuable by a wearer of said glove to provide an indication of the degree of actuation.

19. A glove according to claim 1, in which a plurality of carbon ink sensors are located about the glove.

20. A glove according to claim 1, in which a plurality of sensor pockets are provided about the glove for locating sensors therein.

21. A glove according to claim 18, in which selectable ones of said sensors are arranged to measure opposing directions of bend of a corresponding joint.

22. A glove according to claim 20, in which two or more sensors are arranged in a single sensor pocket, preferably said two or more sensors are arranged over different joints.

23. A glove according to claim 22, in which three sensors are arranged over different joints, preferably said three sensors can be accommodated within single sensor pocket.

24. A glove according to claim 22, in which the sensors are arranged to overlap.

25. A glove according to claim 18, further comprising an insulating layer arranged to electrically isolate a corresponding sensor in use from a wearer.

26. A glove as claimed in claims 18, wherein said sensor or sensors comprise a plurality of independently actuable regions, each being capable of producing respective indications of the degree of actuation thereof.

27. A glove as claimed in claim 1, further comprising capture means for preventing displacement of the dorsal panel finger sections relative to a weaver's digit upon movement of said digit.

28. A glove as claimed in claim 27, wherein said capture means comprises at least one distal phalanx receiving portion extending from a corresponding dorsal panel finger section for receiving an end portion of a corresponding distal phalanx.

29. A glove as claimed in claim 27, wherein said capture means comprises a finger tip portion of a glove or an arcuate member for extending over the end of a finger from the dorsal side to the palmar side of said finger.

30. The glove according to claim 1, in which a sensor is disposed on the portion of the dorsal panel finger section which extends beyond the palmer panel finger section.

* * * * *